United States Patent
Krause et al.

(10) Patent No.: US 9,241,786 B2
(45) Date of Patent: Jan. 26, 2016

(54) METHOD FOR PRODUCING AN INCISION FIGURE FOR A CORNEAL PROSTHESIS

(75) Inventors: Johannes Krause, Nuremberg (DE); Mathias Woelfel, Erlangen (DE)

(73) Assignee: Wavelight GmbH (DE)

( * ) Notice: Subject to any disclaimer, the term of this patent is extended or adjusted under 35 U.S.C. 154(b) by 196 days.

(21) Appl. No.: 13/983,988

(22) PCT Filed: Feb. 15, 2011

(86) PCT No.: PCT/EP2011/000708
§ 371 (c)(1),
(2), (4) Date: Aug. 29, 2013

(87) PCT Pub. No.: WO2012/110048
PCT Pub. Date: Aug. 23, 2012

(65) Prior Publication Data
US 2013/0331935 A1  Dec. 12, 2013

(51) Int. Cl.
*A61F 2/14* (2006.01)
*A61F 9/008* (2006.01)

(52) U.S. Cl.
CPC ............... *A61F 2/143* (2013.01); *A61F 2/142* (2013.01); *A61F 2/148* (2013.01); *A61F 9/0081* (2013.01); *A61F 9/00831* (2013.01); *A61F 9/00836* (2013.01); *A61F 2009/00872* (2013.01)

(58) Field of Classification Search
CPC ......... A61F 2/14; A61F 2/1664; A61F 9/008; A61F 9/0017; A61F 2/142–2/148; A61F 2009/00853; A61F 2009/00872; A61F 2009/00893; A61F 2220/0008; A61F 2250/0058; A61F 2250/0091; A61F 2250/0036; A61F 2250/0037
See application file for complete search history.

(56) References Cited

U.S. PATENT DOCUMENTS

| | | | |
|---|---|---|---|
| 5,549,632 A * | 8/1996 | Lai ..................................... | 606/5 |
| 6,110,166 A * | 8/2000 | Juhasz .............................. | 606/5 |
| 6,221,067 B1 | 4/2001 | Peyman | |
| 6,344,040 B1 * | 2/2002 | Juhasz et al. ...................... | 606/4 |

(Continued)

FOREIGN PATENT DOCUMENTS

| | | |
|---|---|---|
| WO | 2008030699 A2 | 8/2008 |
| WO | 2009158723 A2 | 12/2009 |
| WO | 2012110048 A1 | 8/2012 |

OTHER PUBLICATIONS

Buratto et al.; "The use of the femtosecond laser in penetrating keratoplasty"; American Journal of Ophthalmology; vol. 143, No. 5; pp. 737-742 (Apr. 20, 2007).

(Continued)

*Primary Examiner* — Paul Prebilic

(57) ABSTRACT

Proposed is an apparatus for assistance in the implantation of a corneal prosthesis in a human eye. The apparatus comprises a laser device for providing focussed, pulsed laser radiation, and a control program for the laser device. The control program is designed, to create an incision figure in the tissue of the eye by means of the laser radiation, this incision figure allowing the corneal prosthesis to be inserted. The incision figure in this case comprises a bed incision located entirely in the depth of the corneal material and an annular incision, which, within the circumferential line of the bed incision, extends from the latter, along its entire annular circumference, as far as the corneal anterior surface. The incision figure further may comprise an auxiliary incision, which extends from a location of the eye surface outside the circumferential line of the bed incision as far the bed incision.

8 Claims, 2 Drawing Sheets

(56) References Cited

U.S. PATENT DOCUMENTS

| | | | |
|---|---|---|---|
| 2002/0138069 A1* | 9/2002 | Peyman | 606/5 |
| 2003/0212387 A1* | 11/2003 | Kurtz et al. | 606/4 |
| 2004/0243111 A1* | 12/2004 | Bendett et al. | 606/5 |
| 2004/0243159 A1 | 12/2004 | Shiuey | |
| 2004/0243160 A1 | 12/2004 | Shiuey et al. | |
| 2006/0100612 A1* | 5/2006 | van der Heyd et al. | 606/4 |
| 2007/0244559 A1 | 10/2007 | Shiuey | |
| 2008/0082086 A1* | 4/2008 | Kurtz et al. | 606/4 |
| 2009/0326650 A1* | 12/2009 | Zickler et al. | 623/5.11 |

OTHER PUBLICATIONS

Keramed; KeraKlear Non-Penetrating Artificial Cornea; KeraKlear Artificial Cornea—KeraMed Inc.; http://www.keramed.com/KeraKlear_Artificial_Cornea.html; Jun. 6, 2013.

* cited by examiner

METHOD FOR PRODUCING AN INCISION FIGURE FOR A CORNEAL PROSTHESIS

TECHNICAL FIELD

The invention relates to the implantation of a corneal prosthesis in a human eye.

BACKGROUND

Certain indications (such as, for example, severe opacity, or injuries that heal with possibly severe scar formation) can make it appropriate to replace the affected corneal eye tissue with an artificial implant (prosthesis). Examples of corneal prostheses that can be suitable for such purposes are offered by the firm KeraMed Inc. from Sunnyvale, Calif., under the tradename KeraKlear. As further documentation of examples of corneal prostheses and methods and devices for inserting such prostheses into a human cornea, reference may be made to US 2007/0244559 A1.

SUMMARY OF EXAMPLE EMBODIMENTS

The invention is based on the object of providing a gentle and, at the same time, precise method that can be used in an eye operation in which a corneal prosthesis is implanted in a human eye.

To achieve this object, the invention proposes an apparatus for assistance in the implantation of a corneal prosthesis in a human eye, comprising a laser device for providing focussed, pulsed laser radiation, and a control program for the laser device, the control program being designed, when executed, to cause an incision figure to be produced in the tissue of the eye by means of the laser radiation, the incision figure allowing the corneal prosthesis to be inserted, and comprising a bed incision located entirely in the depth of the corneal material, and further comprising an annular incision, which, within the circumferential line of the bed incision, extends from the latter, along its entire annular circumference, as far as the corneal anterior surface.

The physical effect used in producing incisions by means of laser radiation is that of so-called photodisruption, which is produced as a result of a laser-induced optical breakdown in the tissue of the irradiated material, and which causes tissue to be parted. Each individual radiation pulse can result in such a photodisruption, but the radiation parameters can also be set in such a way that two or more pulses, radiated substantially onto the same location, are necessary in order to exceed the fluence threshold required for a breakdown. Multifarious two-dimensional or three-dimensional incision figures can be produced in the eye tissue through chaining of a multiplicity of photodisruptions. For the patient, laser-assisted production of incisions in the eye is normally less stressful than the mechanical variant, by means of a cutting blade. In addition, laser-produced incisions can be realized with very high precision, which is of great importance, particularly in the case of eye treatments.

In the case of the solution according to the invention, the incision figure produced by means of the laser radiation is designed for an implant that has a prosthesis main portion and at least one support element projecting laterally from the prosthesis main portion. The prosthesis main portion constitutes a type of artificial lens, which comes to lie in the space within the annular incision and constitutes an artificial eye surface there. To enable the prosthesis to be inserted, it is first necessary to remove the piece of tissue that is located between the bed incision and the annular incision and that is separated from the rest of the corneal tissue by these two incisions. An opening is left, which is filled by the prosthesis main portion after the prosthesis has been inserted. As a support element, the prosthesis can have, for example, a circumferential edge that projects substantially with equal width all over from the prosthesis main portion or, alternatively, has a varying projection. It is also conceivable for the prosthesis to have two or more support wings or support fingers, distributed at regular angular intervals around the prosthesis main portion. Irrespective of the number of support elements, each support element, when implanted, extends into that region of the bed incision that is outside the opening remaining after removal of the piece of tissue.

In a preferred development, the incision figure produced by laser technique further comprises an auxiliary incision, which extends, from a location of the eye surface outside the circumferential line of the bed incision, as far the bed incision. This auxiliary incision constitutes an access through which the prosthesis can be inserted in the receiving pocket formed in the cornea. Expediently, at each location the auxiliary incision is narrower than the greatest diameter of the annular incision. For the purpose of insertion, it is then necessary for the prosthesis main portion to be folded together or otherwise collapsed, in order to get the prosthesis through the access channel constituted by the auxiliary incision. Appropriate devices for this purposes are described and shown, for example, in the aforementioned US 2007/0244559 A1. After passing through the auxiliary incision, the prosthesis can unfold (spread out) by itself or, if necessary, with the assistance of the surgeon, and assume its desired seating.

According to a possible embodiment, the bed incision can extend at a substantially constant depth of the corneal material, the auxiliary incision coming continuously closer to the eye surface as its distance from the bed incision increases.

According to a further aspect, the invention provides for a method for implanting a corneal prosthesis in a human eye, comprising the steps of:
providing focussed, pulsed laser radiation,
producing an incision figure in the tissue of the eye by means of the laser radiation, the incision figure comprising a bed incision located entirely in the depth of the corneal material, and further comprising an annular incision, which, within the circumferential line of the bed incision, extends from the latter, along its entire annular circumference, as far as the corneal anterior surface,
removing a piece of corneal tissue delimited by the bed incision and the annular incision,
inserting the corneal prosthesis in the eye in such a way that a main portion of the prosthesis sits in an opening left by the removed piece of tissue, and one or more support elements projecting laterally from the prosthesis main portion extend into the regions of the bed incision located outside the opening.

BRIEF DESCRIPTION OF THE DRAWINGS

The invention is now explained more fully with reference to the appended drawings, wherein.

DETAILED DESCRIPTION OF THE DRAWINGS

Figure 1:
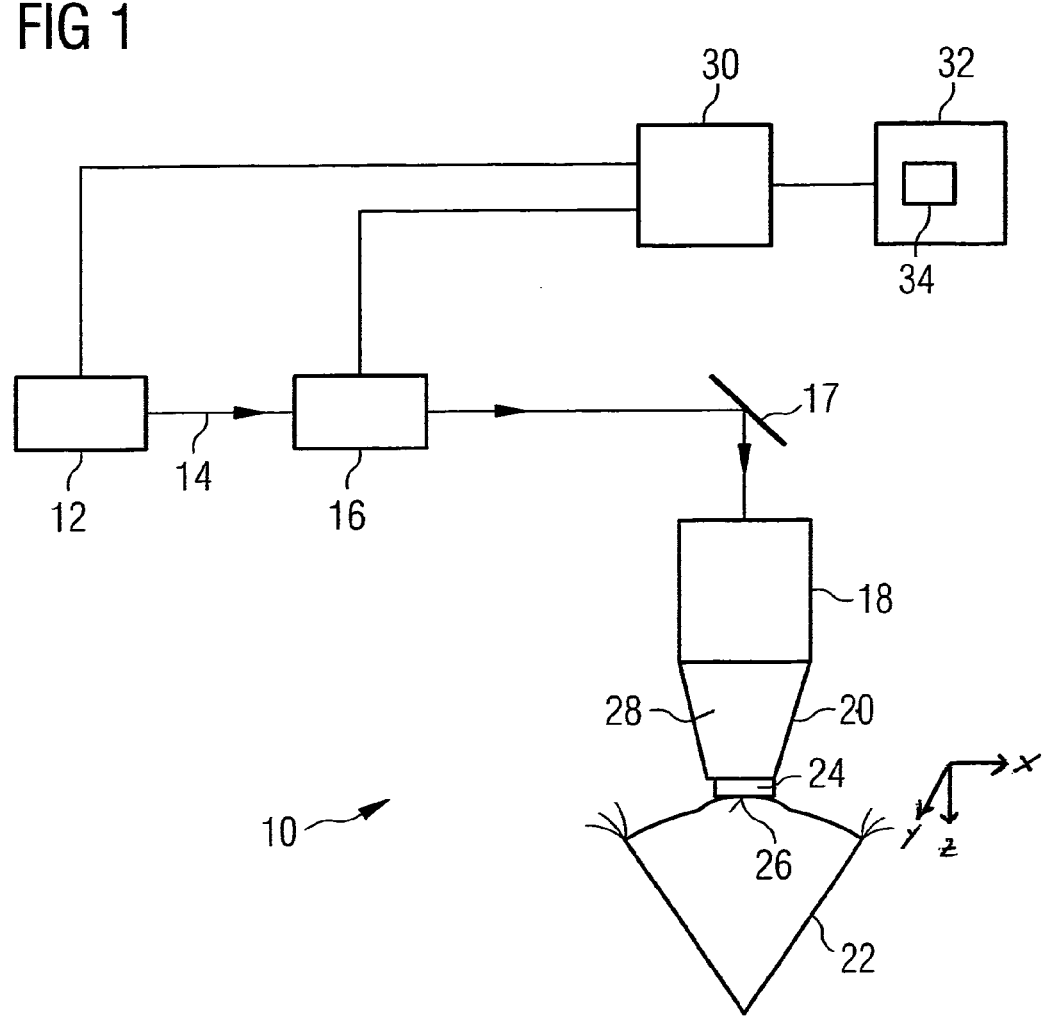
FIG. 1 shows a schematic block representation of an embodiment of a laser device for producing intracorneal incisions.

Reference is first made to FIG. 1. The laser device shown therein, which is denoted in general by 10, comprises a laser source 12, which provides pulsed laser radiation having pulse durations in the femtosecond range, down to the lower picosecond range. From the laser source 12, the laser radiation is emitted in the form of a laser beam 14, in whose beam path a series of components are arranged, including a scanner 16, indicated schematically here as a single-unit function block, an immovable deflection mirror 17 (if appropriate, there may be a multiplicity of such deflection mirrors), and a focussing objective lens 18. The scanner 16 serves for transversal and longitudinal positional control of the focus point of the laser beam 14. Transversal in this case denotes a direction perpendicular to the direction of propagation of the laser beam 14, longitudinal corresponding to the direction of beam propagation. In a usual notation, the transversal plane in the region of the eye can be denoted as an x-y plane, while the longitudinal direction can be denoted as the z direction. A corresponding coordinate cross is shown for elucidation in FIG. 1.

For the purpose of transversal deflection of the laser beam 14, the scanner 16 can comprise, for example, a pair of galvanometrically actuated scanner mirrors, which can be tilted about mutually perpendicular axes. Alternatively, for example, transversal deflection by means of an electro-optical crystal is conceivable. For the z control of the focus position, the scanner 16 can comprise, for example, a lens that can be adjusted longitudinally or that is of variable refractive power, or a deformable mirror, by means of which lens or mirror the divergence of the laser beam 14, and consequently the z position of the beam focus, can be influenced. It is understood that the components of the scanner 16 that serve for transversal focus control and longitudinal focus control can be distributed to differing structural units. For example, the z focus control function can be fulfilled by a lens, which can be arranged in a beam-expanding optical system (beam expander, e.g. Galilean telescope), not represented in greater detail here. The components serving for transversal focus control can be accommodated, for example, in a separate structural unit between the aforementioned beam-expanding optical system and the focussing objective lens 18. The representation of the scanner 16 as a single-unit function block in FIG. 1 thus serves only to assist clarity.

The focussing objective lens 18 is preferably an f-theta objective lens and is preferably detachably coupled, on its beam output side, to a patient adapter 20, which constitutes a bearing interface for the cornea of an eye 22 to be treated. For this purpose, the patient adapter 20 has a contact element 24, which is transparent to the laser radiation and which, on its underside facing towards the eye, has a bearing surface (contact surface) 26 for the cornea. In the exemplary case shown, the bearing surface 26 is realized as a plane surface, and serves to level the cornea, in that the contact element 24 is pressed against the eye 22 with appropriate pressure or the cornea is sucked onto the bearing surface 26 by negative pressure. In the exemplary case shown, the contact element 24 (in the case of plane-parallel realization, usually referred to as an applanation plate) is mounted at the narrower end of a carrier sleeve 28 that widens conically. The connection between the contact element 24 and the carrier sleeve 28 can be non-detachable, for example through adhesive bonding, or detachable, for instance through a screwed connection. In a manner not represented in greater detail, at its wider sleeve end the carrier sleeve 28 has appropriate coupling formations, for coupling on the focussing objective lens 18.

The laser source 12 and the scanner 16 are controlled by a control computer 30, which operates according to a control program 34 stored in a memory 32. The control program 34 contains instructions (program code) which, upon execution by the control computer 30, effect such positional control of the beam focus of the laser beam 14 that an incision figure is produced in the cornea of the eye 22 bearing on the contact element 24, which incision figure is suitable for the subsequent implantation of a corneal prosthesis, which constitutes an artificial eye surface and replaces corneal tissue that is diseased or that otherwise impairs vision.

Figure 2:
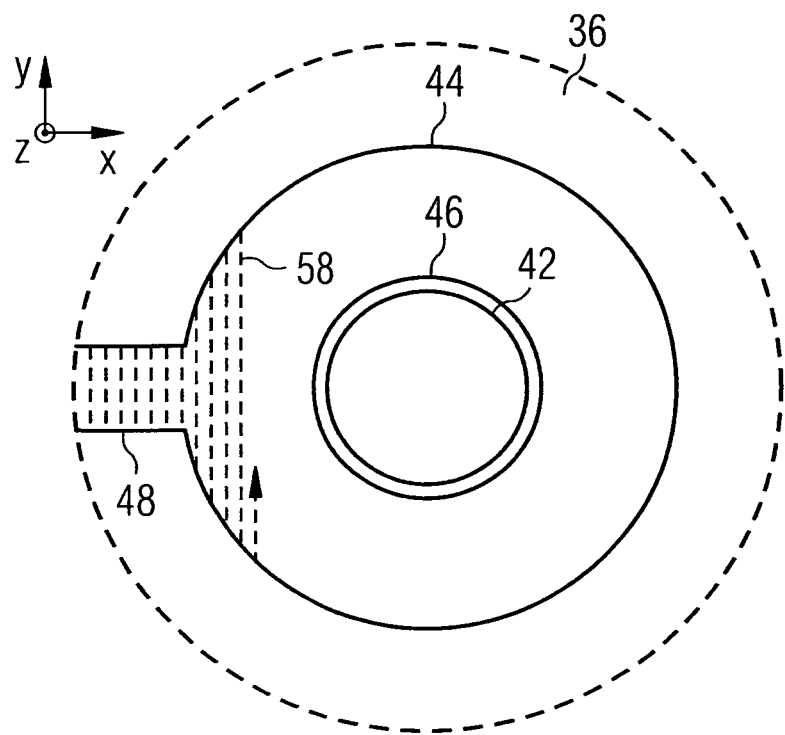
FIG. 2 shows a top view of an incision figure, which can be produced by means of the laser device of FIG. 1 and which is suitable for the implanting of a corneal prosthesis, according to an embodiment.
Figure 3:
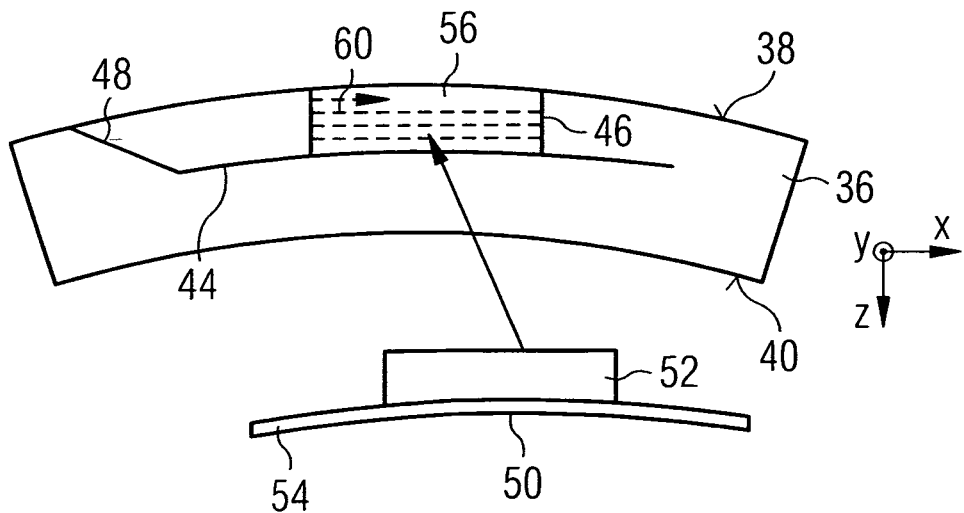
FIG. 3 shows a sectional view of the incision figure of FIG. 2, with a representation of the prosthesis.

To explain an embodiment of this incision figure and of the prosthesis, reference is now additionally made to FIGS. 2 and 3. In these figures, the cornea of the eye 22 to be treated is denoted by 36. It has an anterior surface 38, and a posterior surface 40, which is directed towards the inside of the eye. The broken outer circular line shown in FIG. 2 represents a maximum scanning region enabled by the used laser apparatus in the x-y plane. This maximum scanning region can be referred to as an available scanning region. It is needless to say that a circular maximum x-y scanning region is only exemplary and the available scanning region is not limited to this. In addition, a pupil of the eye is indicated at 42 in FIG. 2.

In the exemplary case of FIGS. 2 and 3, the incision figure produced in the cornea 36 by means of the laser device of FIG. 1 (or, if appropriate, by means of another appropriate laser device) is composed of a bed incision 44, an annular incision 46 and an auxiliary incision 48. The bed incision 44 extends entirely in the depth of the cornea 36, preferably at a substantially constant depth, and has a circular outline in the exemplary case shown. It is understood that, if required, the outline of the bed incision 44 can also have a different shape, depending, in particular, on the outline shape of the corneal prosthesis, shown at 50, which is to be implanted in the cornea 36. Because of the bed incision 44, a pocket is produced, in which the prosthesis 50 can be inserted.

The prosthesis 50 has a main portion 52, and a support edge 54, which is thin in comparison with the latter. The main portion 52 of the prosthesis 50 constitutes, as it were, an artificial lens, intended to replace a diseased or otherwise incurably altered tissue region of the cornea 36. This tissue region is bounded between the bed incision 44 and the annular incision 46, and is to be removed. In FIG. 3, the tissue region to be removed is denoted by 56. The tissue region 56 is separated on all sides from the surrounding corneal tissue by the bed incision 44 and the annular incision 46. For this purpose, the annular incision 46 extends from the bed incision 44 as far as the corneal anterior surface 38, being realized as an annular cylinder in the exemplary case shown. It is understood, however, that, depending on the form of the prosthesis main portion 52, the annular incision 46 can have, for example, a conicity, to a greater or lesser extent. Expediently, the annular incision 46 is so dimensioned that the prosthesis main portion 52 completely fills the space within the annular incision 46, i.e. that the prosthesis 50 can replace completely the piece of tissue 56 to be removed.

Expediently, the circumferential shape of the annular incision 46 depends on the outline shape of the main portion 52 of the prosthesis 50. In the exemplary case shown, the shape of a circular disc is to be assumed for the prosthesis main portion 52, such that the annular incision 46 correspondingly has a circular circumferential course.

The support edge 54 of the prosthesis 50 can project, along the entire circumference of the main portion 52, from the latter in the manner of a hat brim, the projection of the support edge 54 beyond the prosthesis main portion 52 being able to be substantially equal all over, or being able to vary in the circumferential direction. The diameter of the bed incision 44 corresponds, expediently, at least to the maximum diameter of the support edge 54. The annular incision 46 lies radially within the circumferential line of the bed incision 44, according to the projection of the support edge 54 beyond the prosthesis main portion 52, in as much as the bed incision 44 is radically symmetrically with respect to the annular incision 46.

The auxiliary incision 48 constitutes an access channel through which the prosthesis 50 can be inserted into the cornea 36 from the outside. For this purpose, the auxiliary incision 48 produces a connection between the bed incision 44 and the corneal anterior surface 38, the corneal incision, in the exemplary case shown, extending obliquely upwards from the edge of the bed incision 44 to the corneal anterior surface 38. At each location, the width of the auxiliary incision 48 is less than the maximum diameter of the prosthesis main portion 52, this making it necessary to fold together the prosthesis 50, including its main portion 52, to enable it to be implanted through the auxiliary incision 48.

In the exemplary case shown in FIG. 2, the end of the auxiliary incision 48 which is at the anterior surface 38 of the cornea is located directly at the edge of the available x-y scanning region. Of course, this is but one possible example, and in an alternative embodiment this end of the auxiliary incision 48 which is proximate to the surface can be located at a distance from the edge of the available x-y scanning region (i.e. within the broken outer circular line drawn in FIG. 2). In any case, the auxiliary incision 48 extends all the way to the anterior surface 48 of the cornea.

As soon as the prosthesis 50 has reached the bed incision 44, it unfolds, either by itself or with the aid of a tool that can be applied by the surgeon through the auxiliary incision 48 or through the opening produced after removal of the piece of tissue 56. The prosthesis main portion 52 thus spreads out into the aforementioned opening and then, with its upper side, constitutes an artificial eye surface, which, advantageously, adjoins the surrounding regions of the corneal anterior surface 38 in a substantially flush manner.

For the purpose of producing the auxiliary incision 48 and the bed incision 44, the laser device 10 of FIG. 1 (or another appropriate laser device) can use, for example, line scans, as indicated by broken scan lines 58 in FIG. 2. In this case, expediently, the scanning process commences at that end of the auxiliary incision 48 that is located on the corneal anterior surface 38, and then progresses in the direction of the bed incision 44. This direction of progression of the scanning process is also maintained in the case of the bed incision 44, i.e. the bed incision 44 is produced, starting from the area of transition between the auxiliary incision 48 and the bed incision 44 and progressing toward an opposite edge portion of the bed incision 44. The incision figure is preferably produced in the order of the auxiliary incision 48, the bed incision 44 and the annular incision 46. This has the advantage that any gas bubbles, which can be produced during incision, can be discharged to the outside of the eye through an already existing channel and that during incision there is no shadowing of deeper regions of the cornea by less deep incisions.

Superimposed ring-type line scans, as indicated by broken scan lines 60 in FIG. 3, can be used, for example, to produce the annular incision 46. Alternatively, it is conceivable to use a spiral scan. The scanning process can proceed, for example, in the direction from the bed incision 44 to the corneal anterior surface 38 (this variant is sketched in FIG. 3). Alternatively, an inverse direction of the scanning process is conceivable, i.e. from the corneal anterior surface 38 in the direction towards the bed incision 44.

Although this is not represented in FIG. 3, it can be advantageous if the annular incision 46 crosses the bed incision 44 and extends somewhat beyond the latter, in order thus to provide for reliable separation of the piece of tissue 56 from the surrounding corneal tissue.

The invention claimed is:

1. Method for producing an incision figure through which a corneal prosthesis can be inserted into a human eye, comprising:
   providing focussed, pulsed laser radiation,
   producing an incision figure in the tissue of the eye using the laser radiation by:
   producing a bed incision located entirely in the depth of a corneal material,
   producing an annular incision, which, within a circumferential line of the bed incision, extends from the bed incision to a corneal anterior surface, the annular incision produced by scanning the laser radiation with a plurality of superimposed ring scans or a spiral scan from the bed incision to the corneal anterior surface; and
   producing an auxiliary incision through which the corneal prosthesis can be inserted, the auxiliary incision extending from the corneal anterior surface outside the circumferential line of the bed incision to the bed incision, at each location the auxiliary incision being narrower than the greatest diameter of the annular incision.

2. Method for implanting a corneal prosthesis into a human eye, comprising:
   providing focussed, pulsed laser radiation,
   producing an incision figure in the tissue of the eye using the laser radiation by:
   producing a bed incision located entirely in the depth of a corneal material
   producing an annular incision, which, within a circumferential line of the bed incision, extends from the bed incision to a corneal anterior surface, the annular incision produced by scanning the laser radiation with a plurality of superimposed ring scans or a spiral scan from the bed incision to the corneal anterior surface; and
   producing an auxiliary incision through which the corneal prosthesis can be inserted, the auxiliary incision extending from the corneal anterior surface outside the circumferential line of the bed incision to the bed incision, at each location the auxiliary incision being narrower than the greatest diameter of the annular incision;
   folding together the prosthesis before introducing it into the auxiliary incision; and
   unfolding the prosthesis after it has passed through the auxiliary incision.

3. Method according to claim 1, the bed incision extending at a constant depth of the corneal material.

4. Method according to claim 1, wherein producing the auxiliary incision comprises scanning the laser radiation from a first end of the auxiliary incision located at the corneal anterior surface to a second end of the auxiliary incision located at the bed incision.

5. Method according to claim 1, wherein producing the bed incision comprises scanning the laser radiation from an area of transition between the auxiliary incision and the bed incision and to an opposite edge portion of the bed incision.

6. Method according to claim 1, wherein producing the incision figure comprises producing the figure in this order: the auxiliary incision, the bed incision, and the annular incision.

7. Method according to claim 1, further comprising:
   removing a piece of corneal tissue delimited by the bed incision and the annular incision.

8. Method for implanting a corneal prosthesis into a human eye, comprising:
   providing focussed, pulsed laser radiation,
   producing an incision figure in the tissue of the eye using the laser radiation by:
      producing a bed incision located entirely in the depth of a corneal material,
      producing an annular incision, which, within a circumferential line of the bed incision, extends from the bed incision to a corneal anterior surface, the annular incision produced by scanning the laser radiation with a plurality of superimposed ring scans or a spiral scan from the bed incision to the corneal anterior surface; and
   producing an auxiliary incision through which the corneal prosthesis can be inserted, the auxiliary incision extending from the corneal anterior surface outside the circumferential line of the bed incision to the bed incision, at each location the auxiliary incision being narrower than the greatest diameter of the annular incision; and
   inserting the corneal prosthesis into the eye through the auxiliary incision such that a main portion of the prosthesis sits in an opening left by the removed piece of tissue, and one or more support elements projecting laterally from the prosthesis main portion extend into the regions of the bed incision located outside the opening.

\* \* \* \* \*